US012622815B2

(12) United States Patent
Jeong et al.

(10) Patent No.: US 12,622,815 B2
(45) Date of Patent: May 12, 2026

(54) MOLD FOR MANUFACTURING SKIN ATTACHABLE THIN FILM AND METHOD FOR MANUFACTURING SKIN ATTACHABLE THIN FILM BY USING SAME

(71) Applicant: KOREA INSTITUTE OF MACHINERY & MATERIALS, Daejeon (KR)

(72) Inventors: Jun-ho Jeong, Daejeon (KR); Sohee Jeon, Daejeon (KR); Soon-Hyoung Hwang, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 171 days.

(21) Appl. No.: 18/580,690

(22) PCT Filed: Dec. 29, 2021

(86) PCT No.: PCT/KR2021/020225
§ 371 (c)(1),
(2) Date: Jan. 19, 2024

(87) PCT Pub. No.: WO2023/003108
PCT Pub. Date: Jan. 26, 2023

(65) Prior Publication Data
US 2024/0350322 A1      Oct. 24, 2024

(30) Foreign Application Priority Data
Jul. 21, 2021    (KR) ........................ 10-2021-0095533

(51) Int. Cl.
*A61F 13/00*       (2024.01)
*A61F 13/02*       (2006.01)

(52) U.S. Cl.
CPC .. *A61F 13/0276* (2013.01); *A61F 2013/0296* (2013.01)

(58) Field of Classification Search
None
See application file for complete search history.

(56)                References Cited

U.S. PATENT DOCUMENTS

2017/0327963 A1*  11/2017  Chai ........................ B29C 33/40
2019/0117849 A1*   4/2019  Bluecher ................ A61L 31/06

FOREIGN PATENT DOCUMENTS

EP          3243624        11/2017
JP        2011-528029      11/2011
                (Continued)

OTHER PUBLICATIONS

McGrath et al., Determination of parameters for successful spray coating of silicone microneedle arrays, Jun. 1, 2011, International Journal of Pharmaceutics, 415(2011)1410-149 (Year: 2011).*
                (Continued)

*Primary Examiner* — Kim M Lewis
(74) *Attorney, Agent, or Firm* — LEX IP MEISTER, PLLC

(57)                ABSTRACT

Provided is a mold for manufacturing a skin attachable thin film, the mold including: a cast part having a 'U' shape to accommodate a mixed solution in an inner space, and including a lower surface part and a side part, and an inner space accommodating the mixed solution; and at least one protruding pillar protruding from at least a partial region of the lower surface part.

16 Claims, 14 Drawing Sheets

(56) References Cited

FOREIGN PATENT DOCUMENTS

| | | |
|---|---|---|
| JP | 2017-209156 | 11/2017 |
| JP | 2019-158996 | 9/2019 |
| KR | 10-2009-0039724 | 4/2009 |
| KR | 10-2014-0130450 | 11/2014 |
| KR | 20200000145 | 1/2020 |
| WO | 2019225288 | 11/2019 |
| WO | 2020067102 | 4/2020 |

OTHER PUBLICATIONS

EPO, Search Report of EP 21951056.7 dated Jun. 2, 2025, total 4 pages.

* cited by examiner

ACCOMMODATE MIXED SOLUTION IN ACCOMMODATION PART BY SUPPLYING MIXED SOLUTION TO CAST PART — S100

DRY MIXED SOLUTION ACCOMMODATED IN ACCOMMODATION PART FOR MIXED SOLUTION SUPPLIED TO CAST PART TO BE CHANGED INTO SKIN ATTACHABLE THIN FILM — S110

SEPARATE SKIN ATTACHABLE THIN FILM THAT IS FORMED AS DRYING STEP IS PERFORMED FROM CAST PART — S120

S311'

S312'

MOLD FOR MANUFACTURING SKIN ATTACHABLE THIN FILM AND METHOD FOR MANUFACTURING SKIN ATTACHABLE THIN FILM BY USING SAME

TECHNICAL FIELD

The present disclosure relates to a technique for manufacturing a thin film, and particularly, to a mold for manufacturing a skin attachable thin film and a manufacturing method of a skin attachable thin film using the same.

BACKGROUND ART

In generally, most medicines may be orally administered. However, a certain medicine, especially a protein or peptide medicine, may not be effectively adsorbed into a human body by this method due to its intense degradation in the gastrointestinal tract, its poor absorption from an intestinal cell membrane, and/or an interruption of its first-pass by the liver.

Another medicine administration technique may be parenteral injection using a standard syringe or a catheter. Needle injection may cause a needle phobia, a substantial pain, and a local damage to the skin in many patients. Retrieval of a body fluid, such as blood, for a diagnostic purpose may raise a similar concern. In addition, the needle injection may not be ideal for a regular medicine delivery or a regular diagnosis.

Still another medicine delivery technique may use a transdermal delivery method, which usually relies on spread of the medicine across the skin. This method may not be widely used due to poor skin permeability of many medicines. The stratum corneum, which is an outermost layer of the skin, may represent a main barrier to penetration of the transdermal medicine. When the medicine once reaches a dermal depth (i.e., below the epithelium), the medicine may quickly spread to a deeper tissue layer and other parts of the body through blood circulation. In an attempt to improve a rate of protein medicine delivery through the skin, chemical enhancers, iontophoresis, electroporation, ultrasound, and thermal devices have been used to supplement the medicine delivery.

In order to perform the medicine delivery through the skin, it may be necessary to manufacture a thin film capable of being attached to the skin. In general, the thin film may be manufactured in a process of injecting a solution having a low concentration (of 30% or less) into a mold, then drying the same in air, vacuum, blowing, hot air, or the like, separating the thin film from the mold, and cutting the same into a plurality of thin films having a size required for a product.

However, when manufacturing the thin film by using this manufacturing process, the dried thin film in a region of the mold where its bottom and wall surface meet each other may be distorted due to shrinkage or separated from a mold surface.

Accordingly, it may be difficult to perform post-process on the thin film separated from the mold surface, and it may be very difficult to form a precise and flat thin film.

DISCLOSURE

Technical Problem

The present disclosure attempts to provide a mold for manufacturing a plurality of precise and flat thin films, and a manufacturing method of a skin attachable thin film using the same.

The present disclosure also attempts to provide a mold for manufacturing a plurality of thin films without any additional post-process after a drying process, and a manufacturing method of a skin attachable thin film using the same.

The present disclosure also attempts to provide a mold for manufacturing thin films having different thicknesses through a single process, and a manufacturing method of a skin attachable thin film using the same.

The present disclosure also attempts to provide a mold allowing reuse of a solution used in the manufacturing of a skin attachable thin film, and a manufacturing method of a skin attachable thin film using the same.

Technical Solution

According to an embodiment, provided is a mold for manufacturing a skin attachable thin film, the mold including: a cast part accommodating a mixed solution in an inner space; and a protruding pillar formed in the cast part, the skin attachable thin film being manufactured on an upper surface of the protruding pillar, wherein the cast part includes a lower surface part forming a bottom and a side part vertically protruding from an outer peripheral surface of the lower surface part, and a plurality of protruding pillars protrude from the lower surface part.

Here, a first microstructure may be on the upper surface of the protruding pillar.

In addition, the upper surface of the protruding pillar may be a curved surface.

Meanwhile, The mold may further include a first accommodation protrusion protruding from an outer peripheral surface of the upper surface of the protruding pillar.

In addition, the mold may further include a second accommodation protrusion having a polygonal or circular shape and protruding in a closed curve from a region of the lower surface part without the protruding pillar.

In addition, a second microstructure may be formed on a surface of an inner region surrounded by the second accommodation protrusion in the region of the lower surface part without the protruding pillar.

Meanwhile, the cast part may include a plurality of separators disposed between the protruding pillars.

In addition, the cast part may include a plurality of holes capable of being opened and closed that are disposed between the protruding pillars.

According to another embodiment, provided is a manufacturing method of a skin attachable thin film using the mold for manufacturing a skin attachable thin film described above, the method including: a step of accommodating a mixed solution of accommodating the mixed solution in an inner space by supplying the mixed solution to a cast part; a step of drying the mixed solution accommodated in the inner space for the mixed solution supplied to the cast part to be changed into the skin attachable thin film; and a step of acquiring the thin film of separating the skin attachable thin film that is formed as the step of drying the mixed solution is performed from the cast part.

Here, the skin attachable thin film that is acquired in the step of acquiring the thin film may be formed on an upper surface of a protruding pillar.

In addition, the skin attachable thin film that is acquired in the step of acquiring the thin film may be formed in an inner region surrounded by a second accommodation protrusion.

In another example, the method may include: the step of accommodating the mixed solution of accommodating the mixed solution in the inner space by supplying the mixed solution to the cast part; the step of drying the mixed solution accommodated in the inner space for the mixed solution supplied to the cast part to be changed into the skin attachable thin film; a step of coating a functional material of selectively coating the functional material on the skin attachable thin film; a solidification step of drying and solidifying the coated functional material; a step of coating a functional material of selectively coating the functional material on the skin attachable thin film; and the step of acquiring the thin film of separating the skin attachable thin film that is formed as the step of drying the mixed solution is performed in the cast part.

Here, the step of coating the functional material may further include a step of coating an aqueous solution to gather the functional material coated on the skin attachable thin film.

In addition, the step of coating the aqueous solution may further include a step of additionally supplying the mixed solution.

Meanwhile, in the step of acquiring the thin film, the skin attachable thin film may be separated from the cast part by bringing an adhesive film including an adhesive into contact with the cast part.

Here, the adhesive film may separate the plurality of skin attachable thin films by being manufactured to have a length substantially the same as a length of the cast part or have a length shorter than the length of the cast part and greater than a distance between the protruding pillars.

Alternatively, the adhesive film may separate the skin attachable thin film by being manufactured to have a length substantially the same as a length of the protruding pillar or have a length greater than the length of the protruding pillar and shorter than a distance between the protruding pillars.

Advantageous Effects

The mold for manufacturing a skin attachable thin film and the manufacturing method of a skin attachable thin film using the same according to the embodiments of the present disclosure may have the following effects.

First, the plurality of precise and flat thin films may be manufactured using the single mold.

Second, the plurality of thin films may be manufactured without any additional post-process, such as the cutting process after the drying process.

Third, the thin films having the different thicknesses may be manufactured in the single process.

Fourth, the manufacturing cost of the skin attachable thin film may be lower by reusing the solution used in the manufacturing of the skin attachable thin film.

4

Figure 5:
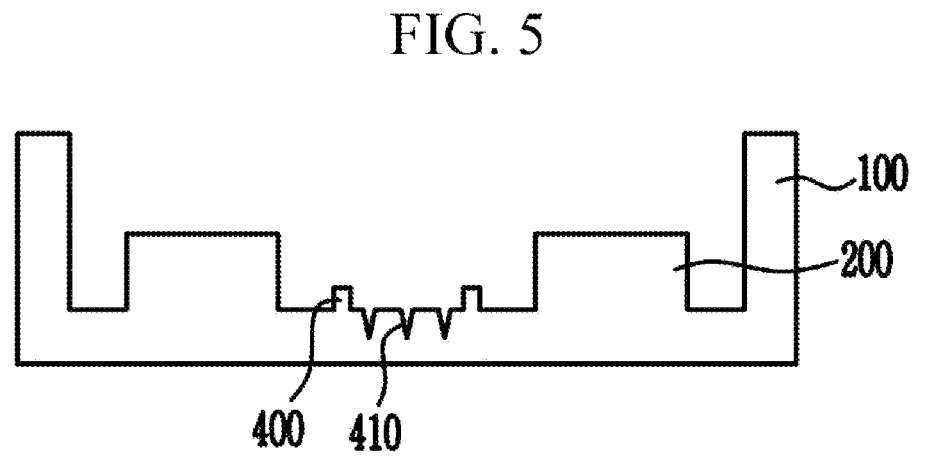

FIG. 5 is a view showing an example of a second microstructure in the third example of the mold for manufacturing a skin attachable thin film according to the present disclosure.

Figure 6:
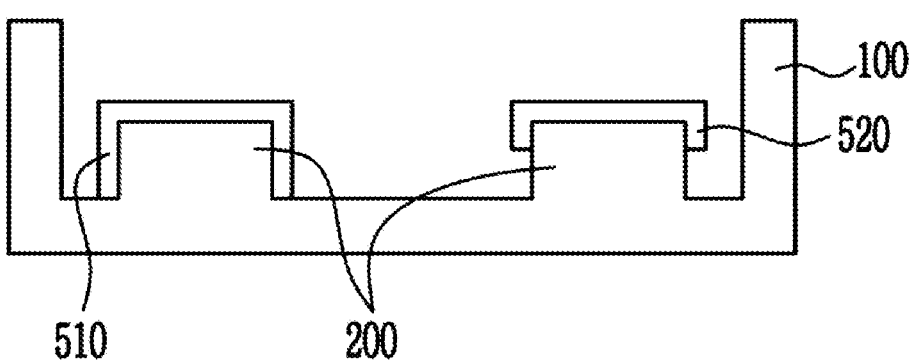

FIG. 6 is a view showing a fourth example of a mold for manufacturing a skin attachable thin film according to the present disclosure.

Figure 7:
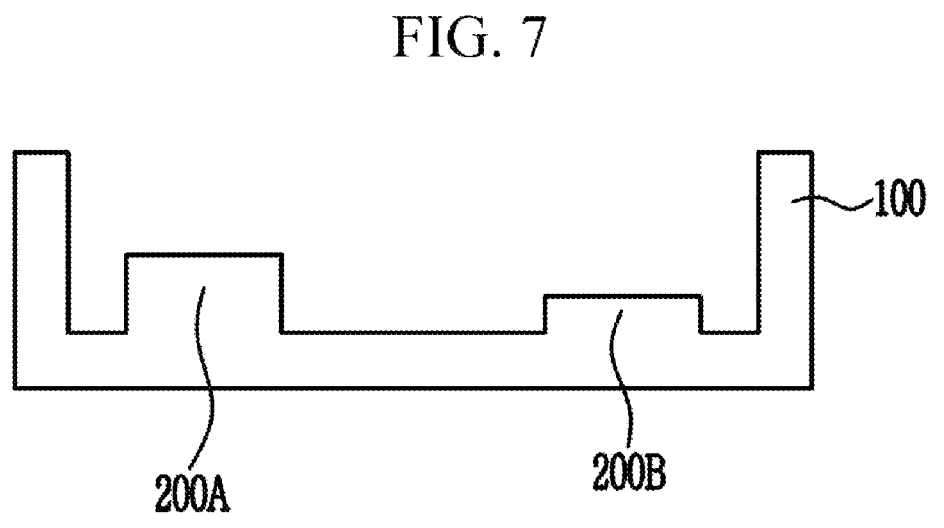

FIG. 7 is a view showing a fifth example of a mold for manufacturing a skin attachable thin film according to the present disclosure.

Figure 8:
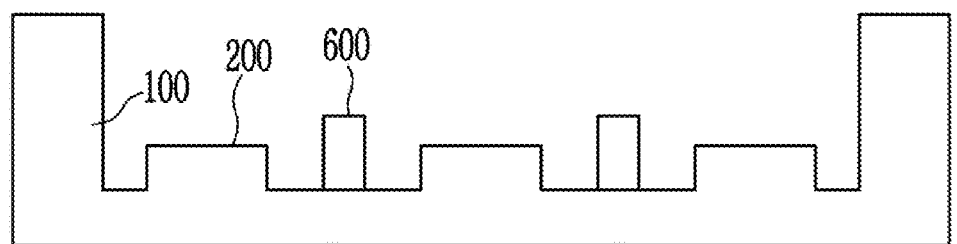

FIG. 8 is a view showing a sixth example of a mold for manufacturing a skin attachable thin film according to the present disclosure.

Figure 9:
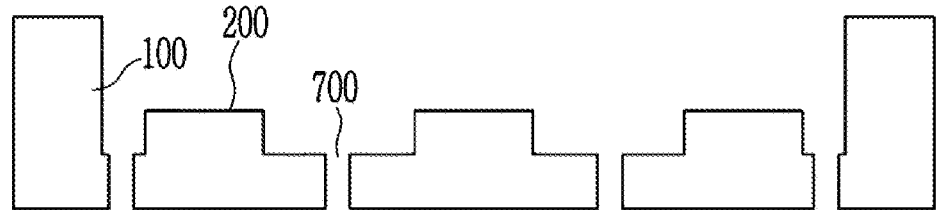

FIG. 9 is a view showing a seventh example of a mold for manufacturing a skin attachable thin film according to the present disclosure.

Figure 10A:
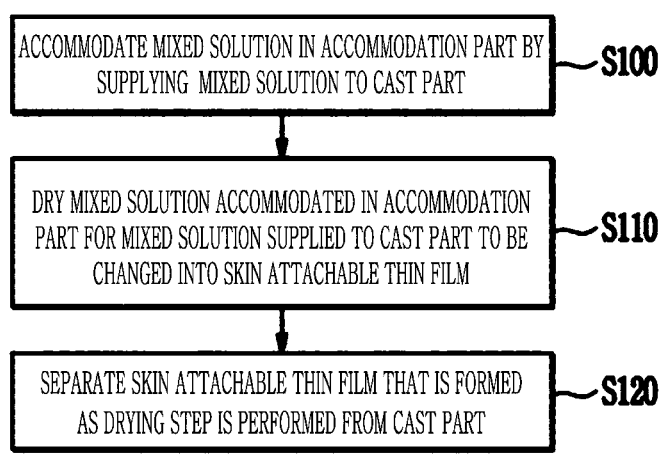
Figure 10B:
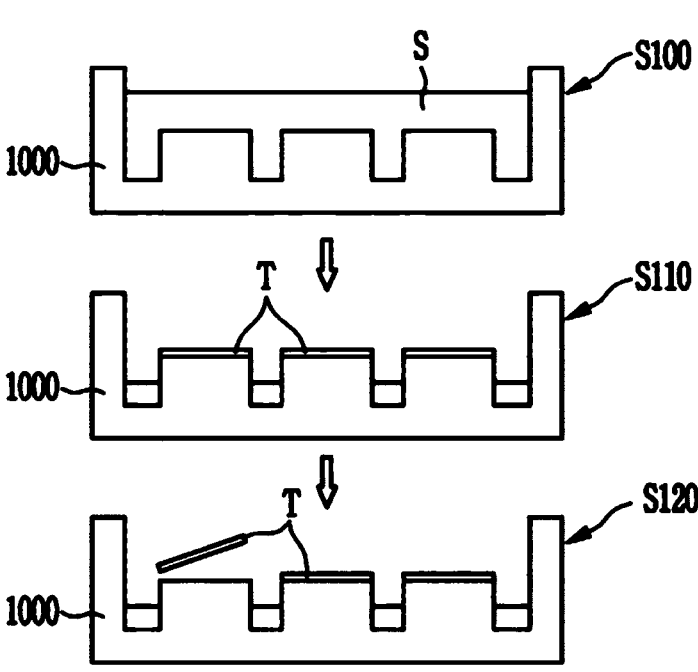

FIGS. 10A and 10B are views showing steps of a manufacturing method of a skin attachable thin film according to the present disclosure.

Figure 11:
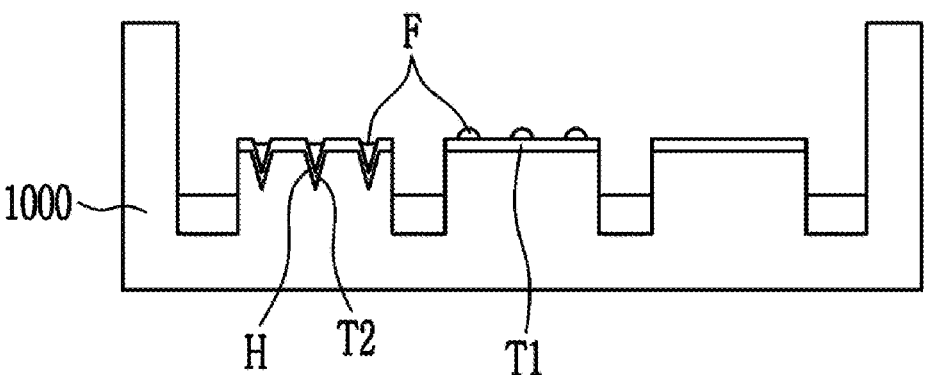

FIG. 11 is a first view showing a step of coating the functional material which may be additionally performed in the manufacturing method of a skin attachable thin film according to the present disclosure.

Figure 12A:
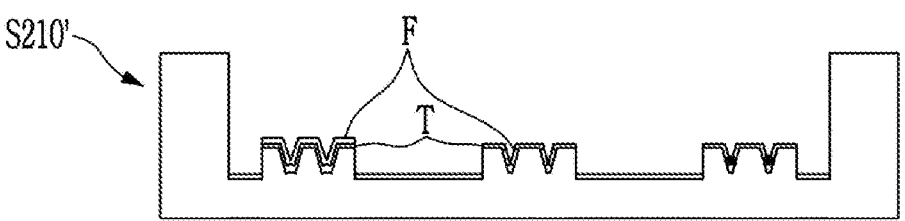
Figure 12B:
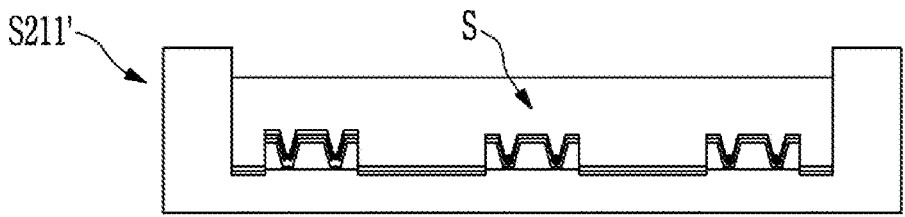
Figure 12C:
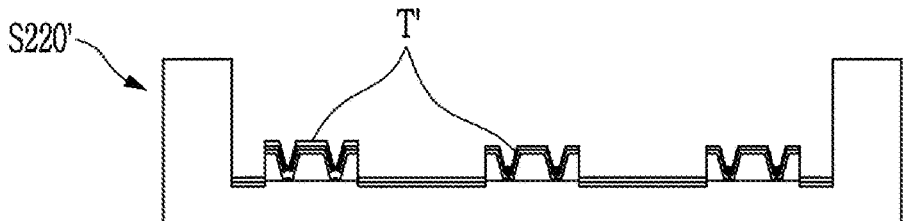

FIGS. 12A, 12B and 12C are second views showing a step of coating the functional material which may be additionally performed in the manufacturing method of a skin attachable thin film according to the present disclosure.

Figure 13A:
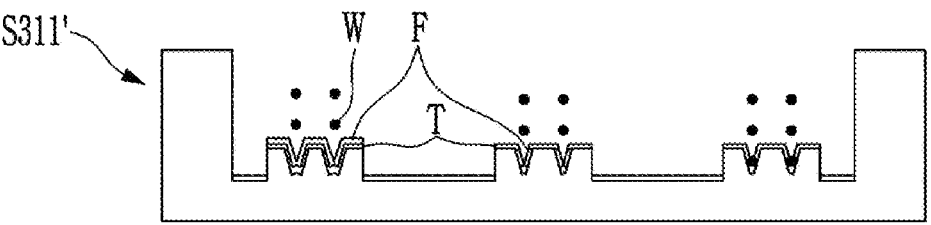
Figure 13B:
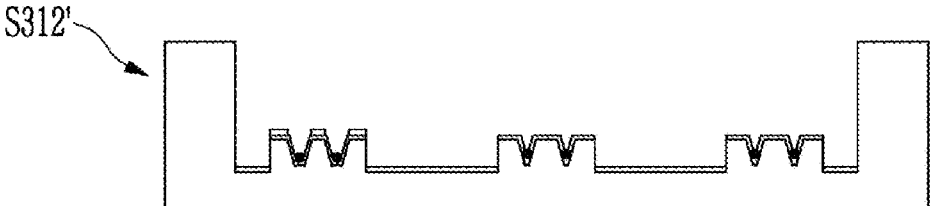

FIGS. 13A and 13B are third views showing a step of coating the functional material which may be additionally performed in the manufacturing method of a skin attachable thin film according to the present disclosure.

Figures 14A, 14B:
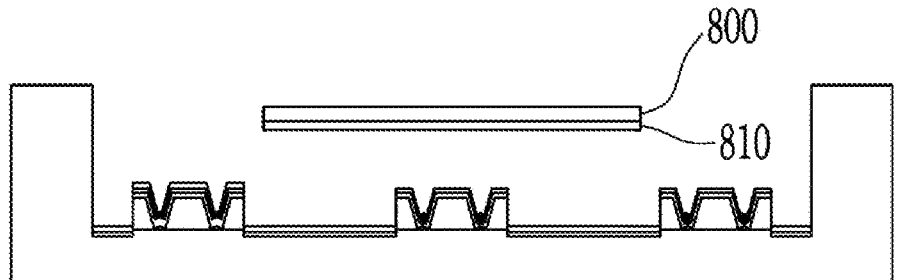

FIGS. 14A and 14B are views showing a step of acquiring the thin film in the manufacturing method of a skin attachable thin film according to the present disclosure.

MODE FOR INVENTION

Hereinafter, the description describes embodiments of the present disclosure for specifically implementing objects of the present disclosure with reference to the accompanying drawings. In describing the embodiments, the same components are denoted by the same names and the same reference numerals, and the following description omits an additional description thereof.

Referring to FIGS. 1A, 1B, 1C, 1D and 2, the description describes a first example of a mold for manufacturing a skin attachable thin film according to the present disclosure as follows.

Figure 1A:
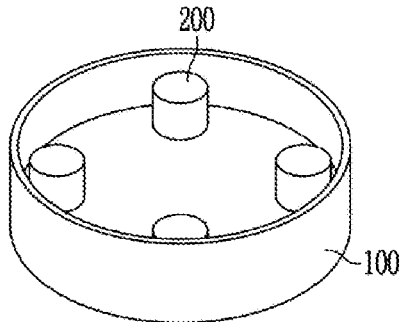
FIGS. 1A, 1B, 1C and 1D are views showing a first example of a mold for manufacturing a skin attachable thin film according to the present disclosure.
Figure 1B:
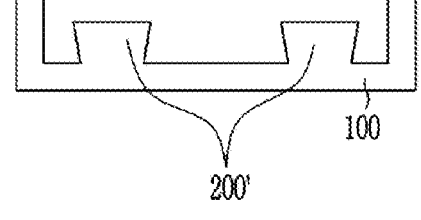
Figure 1C:
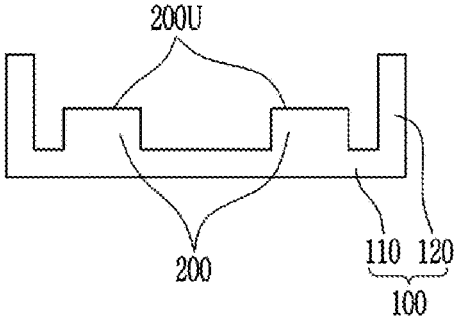
Figure 1D:
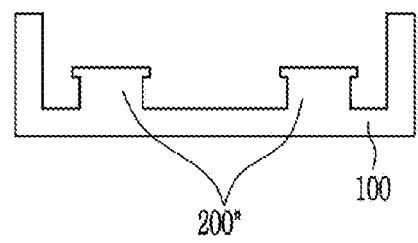
Figure 2:
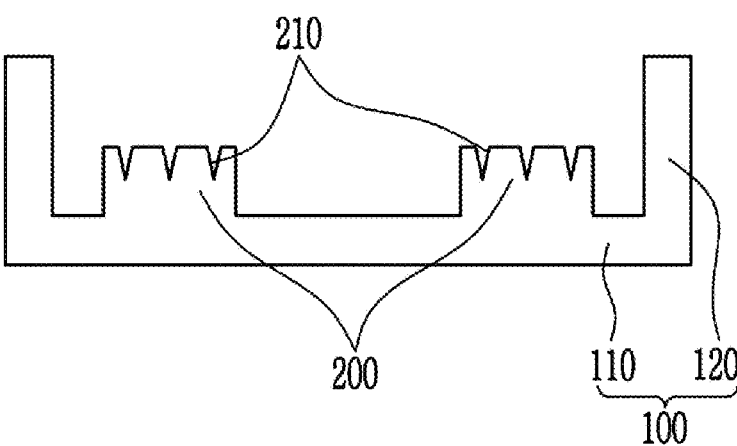
FIG. 2 is a view showing an example of a first microstructure in the first example of the mold for manufacturing a skin attachable thin film according to the present disclosure.

FIGS. 1A, 1B, 1C and 1D are views showing a first example of a mold for manufacturing a skin attachable thin film according to the present disclosure; and FIG. 2 is a view showing an example of a first microstructure in the first example of the mold for manufacturing a skin attachable thin film according to the present disclosure.

First, as shown in FIGS. 1A, 1B, 1C and 1D, the first example of the mold for manufacturing a skin attachable thin film may include a cast part 100 and a protruding pillar 200.

The cast part 100 may include an open upper surface, a 'U'-shaped cross section, a lower surface part 110, and a side part 120 protruding upward from an outer peripheral surface of the lower surface part 110 to accommodate a mixed solution S (in FIGS. 10A and 10B) for manufacturing the skin attachable thin film in an inner space.

A height of the side part 120 may be determined based on the maximum value of a thickness of a skin attachable thin film T (in FIGS. 10A and 10B) to be formed.

The reason is that the thickness of the skin attachable thin film that is described below may be determined based on an amount of mixed solution accommodated in the inner space of the cast part 100, that is, a depth of the mixed solution. Accordingly, the maximum value of the thickness of the skin attachable thin film may be determined based on the height of the side part 120.

The protruding pillar 200 may protrude from at least a partial region of the lower surface part 110, and the cast part 100 may have at least one protruding pillar.

When the plurality of protruding pillars 200 are provided, the skin attachable thin film that is generated as the mixed solution is once accommodated in the inner space of the cast part 100 and goes through a drying process may have the same number as the number of protruding pillars 200.

In this way, according to the present disclosure, the plurality of protruding pillars 200 may be formed on the single mold and the thin film may be manufactured thereon, thereby completing the plurality of skin attachable thin films only in a separation process after drying the thin film. That is, the manufacturing process and cost of the present disclosure may be reduced by eliminating a cutting process.

In addition, when manufacturing the thin film on the bottom of the mold, the dried thin film in a region of the mold where its bottom and wall surface meet each other used to be deformed due to shrinkage, or separated from a surface of the mold, thus making it difficult to form a flat thin film. However, the present disclosure may manufacture a plurality of precise and flat thin films by manufacturing the thin films on the plurality of protruding pillars 200. Furthermore, when manufacturing the thin film on the bottom of the mold, a remaining thin film used to be contaminated or deformed as the thin film goes through the cutting process after the separation, thus making it impossible to reuse the thin film. However, the present disclosure may lower the manufacturing cost of skin attachable thin film by melting and reusing the thin film remaining on the bottom of the mold.

The shape and size of an upper surface 200U of the protruding pillar 200 may be modified to match the shape and size of the skin attachable thin film to be manufactured.

That is, the upper surface of the protruding pillar 200 may have a circular or polygonal shape, thus acquiring the skin attachable thin film to be formed without any restriction on its shape and size.

Here, the upper surface 200U of the protruding pillar 200 may be surface-treated to be hydrophilic. As a result, in a step of drying the mixed solution (S110), the mixed solution may have stability without being separated from the upper surface of the protruding pillar 200 to thus form the skin attachable thin film.

In addition, the upper surface of the protruding pillar 200 may be a flat surface or a curved surface.

Accordingly, the skin attachable thin film may be basically made of a material having flexibility based on a type of the mixed solution, or may also have a shape corresponding to the surface to which the film is attached, thereby increasing its adhesion.

In addition, as shown in FIGS. 1A and 1B, the protruding pillar may have a shape of a cylinder with parallel side surfaces, and as shown in FIGS. 1C and 1D, an area of the upper surface of the protruding pillar may be larger than an area of its lower surface.

That is, as shown in FIG. 1C, a protruding pillar 200' may have a shape of a side surface narrower toward the bottom, and as shown in FIG. 1D, a protruding pillar 200" may have a stepped shape.

As the protruding pillar 200' or 200" has the shape of the area narrower toward the bottom, a region of the lower surface part 110 without the protruding pillar 200' or 200" become larger to secure a larger area where a second accommodation protrusion 400 (in FIGS. 4A and 4B) described below protrude. The second accommodation protrusion is described below.

In addition, as shown in FIG. 2, in the first example of the mold for manufacturing a skin attachable thin film according to the present disclosure, a first microstructure 210 may be formed on the upper surface of the protruding pillar 200.

The first microstructure 210 may be recessed in the upper surface of the protruding pillar 200, a shape of the first microstructure 210 may be freely deformable into a shape enabling accommodation of a coated functional material in a manufacturing method of a skin attachable thin film according to the present disclosure, which is described below, and a diameter of the first microstructure 210 may be several nm to several mm.

Figure 3A:
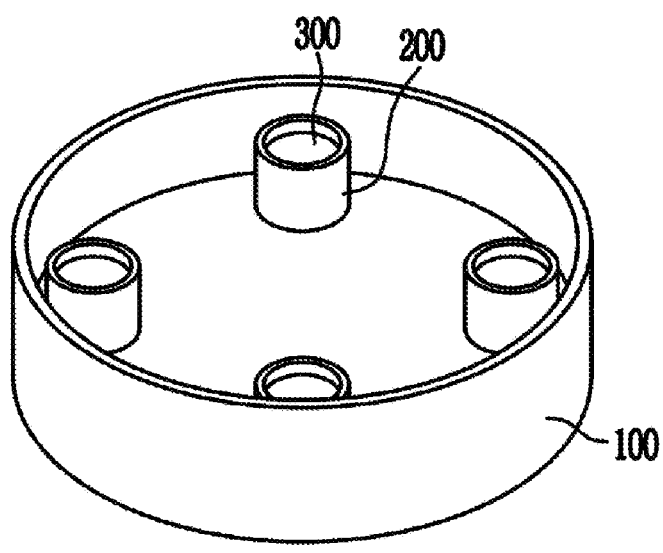
FIGS. 3A and 3B are views showing a second example of a mold for manufacturing a skin attachable thin film according to the present disclosure.
Figure 3B:
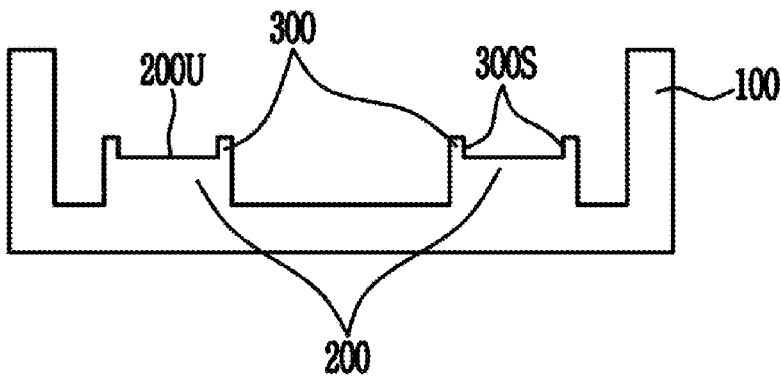

Referring to FIGS. 3A and 3B, the description describes a second example of a mold for manufacturing a skin attachable thin film according to the present disclosure as follows.

The second example of the mold for manufacturing a skin attachable thin film according to the present disclosure may be the same as the first example described above in that at least one protruding pillar 200 is formed on the lower surface part 110 of the cast part 100, and the first microstructure 210 is formed on the upper surface of the protruding pillar 200.

However, the second example of the mold for manufacturing a skin attachable thin film according to the present disclosure that is shown in FIGS. 3A and 3B may further include a first accommodation protrusion 300.

That is, as shown in FIGS. 3A and 3B, the first accommodation protrusion 300 may protrude from an outer peripheral surface of the upper surface of the protruding pillar 200 to thus accommodate the mixed solution in the upper surface of the protruding pillar 200.

Here, the upper surface 200U of the protruding pillar 200 may be hydrophilic, as described above in the first example of the mold for manufacturing a skin attachable thin film according to the present disclosure.

In addition, an inner peripheral surface 300S of the first accommodation protrusion 300 may be hydrophobic to prevent the thin film from being formed on the inner peripheral surface 300S of the first accommodation protrusion 300 when the thin film is dried, thereby preventing the formed skin attachable thin film from being stepped by the first accommodate protrusion 300.

Figure 4A:
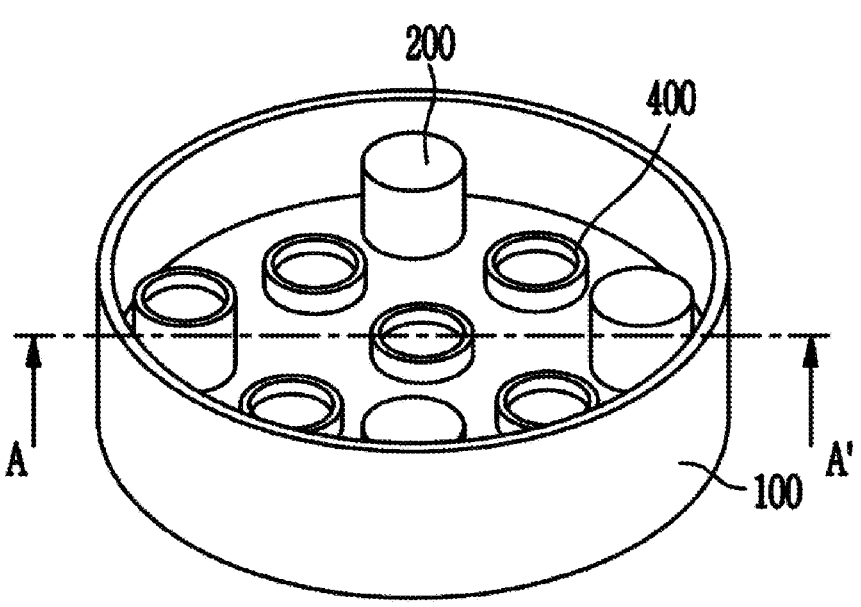
FIGS. 4A and 4B are views showing a third example of a mold for manufacturing a skin attachable thin film according to the present disclosure.
Figure 4B:
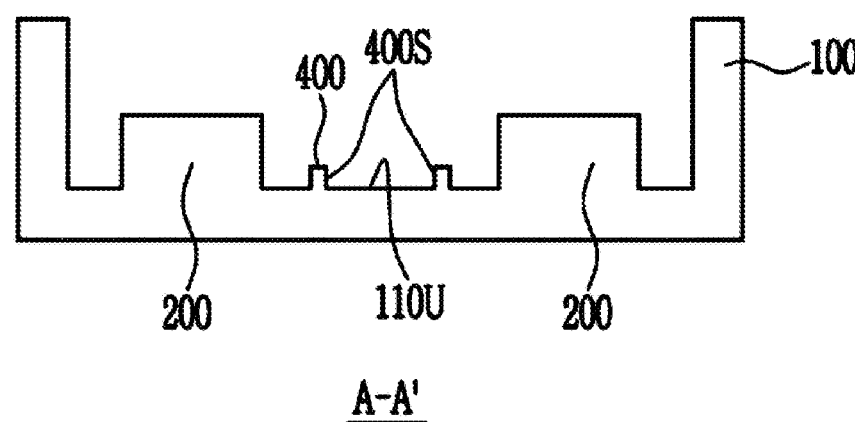

Referring to FIGS. 4A, 4B and 5, the description describes a third example of a mold for manufacturing a skin attachable thin film according to the present disclosure as follows.

The third example of the mold for manufacturing a skin attachable thin film according to the present disclosure may be the same as the first example described above in that at least one protruding pillar 200 is formed from the lower surface part 110 of the cast part 100, and the first microstructure 210 is formed on the upper surface of the protruding pillar 200.

However, the third example of the mold for manufacturing a skin attachable thin film according to the present disclosure that is shown in FIGS. 4A and 4B may further include the second accommodation protrusion 400.

As shown in FIGS. 4A and 4B, the second accommodation protrusion 400 may have the polygonal or circular shape and protruding in a closed curve from the region of the lower surface part 110 without the protruding pillar 200 to accommodate the mixed solution therein.

That is, the skin attachable thin film may be formed not only on the upper surface of the protruding pillar 200 described above, but also in the lower surface part 110 of the cast part 100.

The shape and size of the second accommodation protrusion 400 may be modified to match the shape and size of the skin attachable thin film to be manufactured. As a result, the skin attachable thin film to be formed may be acquired without any restriction on its shape and size.

Here, a surface 110U of an inner region surrounded by the second accommodation protrusion 400 in the region of the lower surface part 110 without the protruding pillar 200 may be hydrophilic like the upper surface 200U of the protruding pillar 200.

In addition, an inner peripheral surface 400S of the second accommodation protrusion 400 may be hydrophobic to prevent the thin film from being formed on the inner peripheral surface 400S of the second accommodation protrusion 400 when the thin film is dried, thereby preventing the formed skin attachable thin film from being stepped by the second accommodate protrusion 400.

In addition, as shown in FIG. 5, in the third example of the mold for manufacturing a skin attachable thin film according to the present disclosure, a second microstructure 410 may be formed in the surface of the inner region surrounded by the second accommodation protrusion 400 in the region of the lower surface part 110 without the protruding pillar 200.

The second microstructure 410 may be recessed in the upper surface of the protruding pillar 200, a shape of the second microstructure 410 may be freely deformable into a shape enabling the accommodation of the coated functional material in the manufacturing method of a skin attachable thin film according to the present disclosure, which is described below, and a diameter of the second microstructure 410 may be several nm to several mm.

Referring to FIG. 6, the description describes a fourth example of a mold for manufacturing a skin attachable thin film according to the present disclosure as follows.

The fourth example of the mold for manufacturing a skin attachable thin film according to the present disclosure may be the same as the first example described above in that at least one protruding pillar 200 is formed from the lower surface part 110 of the cast part 100, and the first microstructure 210 is formed on the upper surface of the protruding pillar 200.

However, the fourth example of the mold for manufacturing a skin attachable thin film according to the present disclosure that is shown in FIG. 6 may further include a pillar fitting block 510 or 520.

As shown in FIG. 6, the pillar fitting block 510 or 520 may be inserted into the protruding pillar 200 to acquire a skin attachable thin film that has a size larger than the size of the skin attachable thin film that is capable of being manufactured from the protruding pillar 200.

That is, the pillar fitting block 510 or 520 may have an inner diameter that is the same as or slightly larger than an outer diameter of the protruding pillar 200 to thus be inserted into the protruding pillar 200, and the pillar fitting block 510 or 520 may have an outer diameter larger than the outer diameter of the protruding pillar 200.

Here, an upper surface of the pillar fitting block 510 or 520 may be the flat surface or the curved surface, the upper surface of the pillar fitting block 510 or 520 may have various shapes, and a third microstructure (not shown)

performing the same function as the first and second microstructures 210 and 410 described above may be formed on the upper surface of the pillar fitting block 510 or 520.

In addition, a third accommodation protrusion (not shown) performing the same function as the first and second accommodation protrusions 300 and 400 described above may be formed on the upper surface of the pillar fitting block.

In addition, the pillar fitting block may have a length to entirely cover the side surface of the protruding pillar 200 (in the case of the pillar fitting block 510), or have a length to cover only a portion of an upper part of the protruding pillar 200 (in the case of the pillar fitting block 520) not to interfere with the generation of the skin attachable thin film that is formed by the second accommodation protrusion 400 formed on the lower surface part 110 of the cast part 100.

As a result, the pillar fitting block 510 or 520 may be selectively inserted into the protruding pillar 200, thus making it possible to acquire thin films having different sizes in a single process.

Referring to FIG. 7, the description describes a fifth example of a mold for manufacturing a skin attachable thin film according to the present disclosure as follows.

The fifth example of the mold for manufacturing a skin attachable thin film according to the present disclosure may be the same as the first example described above in that at least one protruding pillar 200 is formed from the lower surface part 110 of the cast part 100, and the first microstructure 210 is formed on the upper surface of the protruding pillar 200.

However, in the fifth example of the mold for manufacturing a skin attachable thin film according to the present disclosure, the protruding pillar may include a first protruding pillar 200A and a second protruding pillar 200B.

As shown in FIG. 7, the first protruding pillar 200A and the second protruding pillar 200B may have different heights, and the thickness of the formed skin attachable thin film may be changed based on a height difference between the first protruding pillar 200A and the second protruding pillar 200B.

That is, the skin attachable thin films that have different thicknesses may be generated through the single process in the fifth example of the mold for manufacturing a skin attachable thin film according to the present disclosure.

Referring to FIG. 8, the description describes a sixth example of a mold for manufacturing a skin attachable thin film according to the present disclosure as follows.

The sixth example of the mold for manufacturing a skin attachable thin film according to the present disclosure may be the same as the first example described above in that at least one protruding pillar 200 is formed from the lower surface part 110 of the cast part 100, and the first microstructure 210 is formed on the upper surface of the protruding pillar 200.

However, the sixth example of the mold for manufacturing a skin attachable thin film according to the present disclosure that is shown in FIG. 8 may further include a plurality of separators 600.

Here, the separator 600 may be formed not only between the protruding pillars 200, but also between a side wall of the cast part 100 and the protruding pillar 200. In addition, the separator 600 may prevent the mixed solution that is changed into the skin attachable thin film from being deformed due to the shrinkage in the step of drying the mixed solution described below. Here, a height of the separator 600 may not exceed a height of the cast part 100.

On the other hand, the separator 600 may not only prevent the mixed solution from being deformed, but also function as the protruding pillar 200 by forming the microstructure in an upper surface of the separator 600. That is, more skin attachable thin films may be acquired when the separator 600 is used as the protruding pillar 200.

Referring to FIG. 9, the description describes a seventh example of a mold for manufacturing a skin attachable thin film according to the present disclosure as follows.

The seventh example of the mold for manufacturing a skin attachable thin film according to the present disclosure may be the same as the first example described above in that at least one protruding pillar 200 is formed from the lower surface part 110 of the cast part 100, and the first micro-structure 210 is formed on the upper surface of the protruding pillar 200.

However, the seventh example of the mold for manufacturing a skin attachable thin film according to the present disclosure that is shown in FIG. 9 may further include a plurality of holes 700 capable of being opened and closed.

Here, the plurality of holes 700 capable of being opened and closed may be formed not only between the protruding pillars 200, but also between the side wall of the cast part 100 and the protruding pillar 200. In addition, the plurality of holes 700 capable of being opened and closed may enable the mixed solution to be reused by controlling its opening and closing before the mixed solution is dried in a step of accommodating the mixed solution described below to thus discharge the mixed solution to the outside of the cast part 100.

That is, the plurality of holes 700 capable of being opened and closed may enable the mixed solution to be reused even though the same amount of mixed solution is used to manufacture the skin attachable thin film, thereby enabling a larger amount of the skin attachable thin film to be manufactured.

The configurations of the mold for manufacturing a skin attachable thin film in the first to seventh examples of the present disclosure described above may be not only used in one embodiment, but also used in other embodiments with different configurations for the respective examples.

The description describes a manufacturing method of a skin attachable thin film according to the present disclosure as follows.

As shown in FIGS. 10A and 10B, the manufacturing method of a skin attachable thin film according to the present disclosure uses a mold 1000 for manufacturing a skin attachable thin film according to the first to seventh examples of the present disclosure, and reference numerals indicating the components of the mold 1000 for manufacturing a skin attachable thin film are the same as those described with reference to FIGS. 1A to 9.

In detail, the manufacturing method of a skin attachable thin film according to the present disclosure may include a step of accommodating the mixed solution (S100), the step of drying the mixed solution (S110), and a step of acquiring the thin film (S120).

In the step of accommodating the mixed solution (S100), the mixed solution S may be accommodated in the inner space by supplying the mixed solution S to the cast part 100.

In the step of accommodating the mixed solution (S100), the mixed solution S may be vacuum treated while being accommodated in the cast part 100. An accommodation state of the mixed solution S in the cast part 100 may be stabilized by the vacuum treatment, an air bubble in the mixed solution S may be removed, or drying of the mixed solution S may be promoted. In addition, the mixed solution S may be vacuum treated before being supplied to the cast part 100.

Here, a solute in the mixed solution S may be a material which may be dissolved or decomposed in a living body. The solute may consist of the following groups: nucleic acid, deoxyribonucleic acid (DNA), ribonucleic acid (RNA), polydeoxyribonucleotide (PDRN), hyaluronic acid, alginic acid, pectin, carrageenan, chondroitin (sulfate), chondroitin sulfate, glycogen, dextran (sulfate), dextran, dextrin, chitosan, polylysine, collagen, gelatin, carboxymethyl chitin, fibrin, agarose, pullulan polylactide, polyglycolide (PGA), polylactide-glycolide copolymer (PLGA), hyaluronic acid, alginic acid, pectin, carrageenan, chondroitin (sulfate), dextran (sulfate), chitin, chitosan, polylysine, collagen, gelatin, polysaccharides such as carboxymethyl chitin, fibrin, agarose, and pullulan, proteins such as collagen, gelatin, and their hydrolysates, pullulan polyanhydride, polyortheoester, polyetherester, polycaprolactone, polyesteramide, poly(butyric acid), poly(valeric acid), polyurethane, polyacrylate, ethylene-vinyl acetate polymers, acrylic substituted cellulose acetate, non-degradable polyurethanes, polystyrene, polyvinyl chloride, polyvinyl fluoride, poly(vinyl imidazole), chlorosulphonatepolyolefins, polyethylene oxide, polyvinylpyrrolidone (PVP), polyvinyl alcohol, polyethylene glycol (PEG), polymethacrylate, polyacrylic acid, carboxyvinyl polymer, hydroxypropyl methylcellulose, ethylcellulose (EC), hydroxypropylcellulose (HPC), carboxymethylcellulose, cyclodextrin, and the copolymers of the monomers and celluloses that form these polymers.

In addition, the solute of the mixed solution S may include a material that may be dissolved in both of a volatile inorganic solvent such as water and an organic solvent such as ethanol, acetone, ether, or benzene.

In the step of drying the mixed solution (S110), the mixed solution S accommodated in the inner space may be dried for the mixed solution S supplied to the cast part 100 to be changed into a skin attachable thin film T.

In the step of drying the mixed solution (S110), the cast part 100 accommodating the mixed solution S may be dried using air, vacuum, blowing, hot air, or the like at a certain drying temperature for a certain drying time in a separate drying unit (not shown).

A drying method performed in the step of drying the mixed solution (S110) is not limited to the method described above, and may be performed using a usable drying method.

The drying temperature and the drying time in the step of drying the mixed solution (S110) may be adjusted based on a type of the mixed solution S and a capacity of the mixed solution S accommodated in the cast part 100.

In addition, in the step of drying the mixed solution (S110), the bubble in the mixed solution S accommodated in the cast part 100 may be removed through a pipetting unit (not shown) to generate the high-quality skin attachable thin film T.

In the step of acquiring the thin film (S120), the skin attachable thin film T that is formed as the step of drying the mixed solution (S110) is performed may be separated from the cast part 100.

In the step of acquiring the thin film (S120), the thin film T may be separated using a separate adhesive film. This configuration is described below.

In addition, the skin attachable thin film T that is acquired in the step of acquiring the thin film (S120) may not only be the skin attachable thin film T that is formed on the upper surface of the protruding pillar 200, that is, the inner region surrounded by the second accommodation protrusion 400, but also be the skin attachable thin film T that is formed on the upper surface of the pillar fitting block 510 or 520.

In addition, the manufacturing method of a skin attachable thin film according to the present disclosure may further include a step of coating the functional material (S110') and a solidification step (not shown).

The step of coating the functional material (S110') may preferably be performed after the step of drying the mixed solution (S110). In the step of coating the functional material (S110'), the mixed solution S or a functional heterogeneous material (hereinafter, referred to as a functional material F) may be selectively coated on an upper surface of the skin attachable thin film T.

Here, the functional material F may include a material exhibiting a medicinal, mechanical, or electrochemical property exhibiting an effective property of a human body.

As shown in FIG. 11, in the step of coating the functional material (S110'), the functional material F may be selectively coated on an upper surface of a flat skin attachable thin film T1 that is formed on the upper surface of the protruding pillar 200 shown in FIG. 1A, 1B, 1C and 1D, or may be selectively coated in a groove part H formed in a skin attachable thin film T2 by the first microstructure to the third microstructure.

Next, in the solidification step, the functional material F coated on the skin attachable thin film T1 or T2 may be dried and solidified, and the step of acquiring the thin film (which is the same as the step S120 in FIGS. 10A and 10B) may then be performed, thereby acquiring the skin attachable thin film T1 or T2 that includes the functional material F.

As shown in FIG. 11 and FIGS. 12A to 12C, in the step of coating the functional material, the functional material F may be selectively coated on the upper surface of the flat skin attachable thin film T1 that is formed on the upper surface of the protruding pillar 200 shown in FIG. 1A, 1B, 1C and 1D, or may be selectively coated in the groove part H formed in the skin attachable thin film T2 by the first microstructure to the third microstructure.

However, unlike the fact that the solidification step is performed after the functional material is coated in the example of FIG. 11, in the examples of FIGS. 12A to 12C, the functional material may be coated (S210'), and a step of accommodating the mixed solution S in the cast part 100 (S211') may then be performed again.

That is, in the examples of FIGS. 12A to 12C, the mixed solution S may be accommodated again and a step of acquiring the thin film (S220', which is the same as the step S120 in FIGS. 10A and 10B) may then be performed to thus acquire not only the skin attachable thin film T that is disposed under the functional material F but also a skin attachable thin film T' that is disposed on the functional material F, thereby acquiring more skin attachable thin films.

Referring to FIG. 11 to FIGS. 13A and 13B, in the step of coating the functional material (which is the same as the step S210' in FIGS. 12A, 12B and 12C), the functional material F may be selectively coated on the upper surface of the flat skin attachable thin film T1 that is formed on the upper surface of the protruding pillar 200 shown in FIGS. 1A, 1B, 1C and 1D, or may be selectively coated in the groove part H formed in the skin attachable thin film T2 by the first microstructure to the third microstructure.

However, unlike the fact that the step of accommodating the mixed solution S in the cast part 100 is performed again after the functional material is coated in the example of FIGS. 12A, 12B and 12C, in the examples of FIGS. 13A and 13B, the functional material may be coated (which is the same as the step of S210' in FIGS. 12A, 12B and 12C), and a step of coating an aqueous solution W (S311') may then be performed on the functional material. Here, the step of coating the aqueous solution (S311') may be performed before the functional material is dried.

That is, in the examples of FIGS. 13A and 13B, the aqueous solution W may be coated on the functional material F, thereby gathering the functional material coated on the skin attachable thin film T (S312'). For example, the functional material F may be coated in the groove part H formed in the skin attachable thin film T2 by the first to third microstructures of the protruding pillar 200 shown in FIGS. 1A, 1B, 1C and 1D. In this case, the aqueous solution W may gather the functional material F to an end of the groove part H.

When the skin attachable thin film T2 is separated from the mold and attached to the skin, the groove part H formed in the skin attachable thin film T2 may be inserted into the skin and then be dissolved to deliver the functional material F including the groove part H to the skin. The aqueous solution W may gather the functional material F to the end of the groove part H, thereby delivering the functional material F deep into the skin. Here, the aqueous solution W may be evaporated while going through a step of drying the functional material. In the examples of FIGS. 13A and 13B, the mixed solution S may be accommodated again after the step of coating the aqueous solution (S311'), and the step of acquiring the thin film (which is the same as the step S220' in FIGS. 12A, 12B and 12C) may be performed to thus acquire not only the skin attachable thin film T that is disposed under the functional material F but also the skin attachable thin film T' that is disposed on the functional material F, thereby acquiring more skin attachable thin films.

Referring to FIGS. 11 to 14B, in the manufacturing method of a skin attachable thin film according to the present disclosure, in the step of acquiring the thin film (which is the same as S120 in FIGS. 10A and 10B), the skin attachable thin film T, T1, T2 or T' may be separated from the cast part 100 by bringing an adhesive film 800 including an adhesive 810 into contact with the cast part 100.

Here, the adhesive film 800 may simultaneously acquire the plurality of skin attachable thin films that are formed on the upper surfaces of the protruding pillars 200 of the cast part 100 by having a length substantially the same as a length of the cast part 100, or having a length shorter than the length of the cast part 100 and greater than a distance between the protruding pillars 200.

However, the adhesive film 800 is not limited thereto, and may acquire only one skin attachable thin film that is formed on the upper surface of the protruding pillar 200 of the cast part 100 by having a length substantially the same as the length of the protruding pillar 200, or having a length greater than the length of the protruding pillar 200 and shorter than the distance between the protruding pillars 200.

As described above, the present disclosure is not limited to the above-mentioned specific embodiments, and may be variously modified by those skilled in the art to which the present disclosure pertains without departing from the scope and spirit of the present disclosure as disclosed in the accompanying claims. These modifications should also be understood to fall within the scope of the present disclosure.

The invention claimed is:

1. A mold for manufacturing a skin attachable thin film, the mold comprising:

a cast part accommodating a mixed solution in an inner space; and a plurality of protruding pillars in the cast part, the skin attachable thin film being manufactured on an upper surface of the protruding pillars; and a pillar accommodation protrusion protruding in a closed curve from an outer peripheral surface of the upper surface of the protruding pillars and having a polygonal or circular shape, wherein the cast part includes a lower surface part forming a bottom and a side part vertically protruding from an outer peripheral surface of the lower surface part, and the plurality of protruding pillars protrude from the lower surface part.

2. The mold of claim 1, wherein a pillar microstructure is on the upper surface of the protruding pillars.

3. The mold of claim 1, wherein the upper surface of the protruding pillars is a curved surface.

4. The mold of claim 1, wherein the cast part includes a plurality of holes capable of being opened and closed that are disposed between the protruding pillars.

5. A manufacturing method of a skin attachable thin film using the mold for manufacturing a skin attachable thin film according to claim 1, the method comprising:

accommodating the mixed solution in an inner space by supplying the mixed solution to the cast part;

drying the mixed solution accommodated in the inner space for the mixed solution supplied to the cast part to be changed into the skin attachable thin film; and separating the skin attachable thin film that is formed as the drying the mixed solution is performed from the cast part.

6. The method of claim 5, wherein the skin attachable thin film that is acquired in the separating the thin film is formed on an upper surface of a protruding pillar.

7. The method of claim 5, wherein the skin attachable thin film that is acquired in the separating the thin film is formed in an inner region surrounded by an accommodation protrusion.

8. The method of claim 5, further comprising:

between the drying the mixed solution and the separating the thin film, selectively coating a functional material on the skin attachable thin film; and drying and solidifying the coated functional material.

9. The method of claim 8, wherein the coating the functional material further includes coating an aqueous solution to gather the functional material coated on the skin attachable thin film.

10. The method of claim 9, wherein the coating the aqueous solution further includes additionally supplying the mixed solution.

11. The method of claim 8, wherein in the separating the thin film, the skin attachable thin film is separated from the cast part by bringing an adhesive film including an adhesive into contact with the cast part.

12. The method of claim 11, wherein the adhesive film separates the plurality of skin attachable thin films by being manufactured to have a length substantially the same as a length of the cast part or have a length shorter than the length of the cast part and greater than a distance between the protruding pillars.

13. The method of claim 11, wherein the adhesive film separates the skin attachable thin film by being manufactured to have a length substantially the same as a length of the protruding pillar or have a length greater than the length of the protruding pillar and shorter than a distance between the protruding pillars.

14. A mold for manufacturing a skin attachable thin film, the mold comprising:

a cast part accommodating a mixed solution in an inner space; and a plurality of protruding pillars in the cast part, the skin attachable thin film being manufactured on an upper surface of the protruding pillars; and a lower surface accommodation protrusion having a polygonal or circular shape and protruding in a closed curve from a region of the lower surface part without the protruding pillars, wherein the cast part includes a lower surface part forming a bottom and a side part vertically protruding from an outer peripheral surface of the lower surface part, and the plurality of protruding pillars protrude from the lower surface part.

15. The mold of claim 14, wherein a lower surface microstructure is formed on a surface of an inner region surrounded by the lower surface accommodation protrusion in the region of the lower surface part without the protruding pillars.

16. A mold for manufacturing a skin attachable thin film, the mold comprising:

a cast part accommodating a mixed solution in an inner space; and a plurality of protruding pillars in the cast part, the skin attachable thin film being manufactured on an upper surface of the protruding pillars, wherein the cast part includes a lower surface part forming a bottom and a side part vertically protruding from an outer peripheral surface of the lower surface part, the plurality of protruding pillars protrude from the lower surface part, and the cast part includes a plurality of separators disposed between the protruding pillars.

* * * * *